United States Patent [19]

Stepanski et al.

[11] Patent Number: 5,164,166
[45] Date of Patent: Nov. 17, 1992

[54] APPARATUS FOR DISINFECTING CONTACT LENSES USING MICROWAVE ENERGY

[75] Inventors: Stephen F. Stepanski, Rochester; Kelvin H. Wildman, Webster, both of N.Y.

[73] Assignee: Bausch & Lomb Incorporated, Rochester, N.Y.

[21] Appl. No.: 513,324

[22] Filed: Apr. 20, 1990

[51] Int. Cl.$^5$ .............................. A61L 2/12; H05B 6/64
[52] U.S. Cl. ................................. 422/297; 422/301; 422/21; 422/102; 134/901; 206/5.1; 219/10.55 R; 219/10.55 F; 250/455.1
[58] Field of Search .............. 422/297, 102, 104, 292, 422/300, 301, 21; 250/455.1; 206/5.1; 220/400, 410, 501; 219/10.55 R, 10.55 A, 10.55 F

[56] References Cited

U.S. PATENT DOCUMENTS

| | | | |
|---|---|---|---|
| 3,939,968 | 2/1976 | Ryder | 206/5.1 |
| 4,400,357 | 8/1983 | Hohmann | 422/297 |
| 4,593,169 | 6/1986 | Thomas | 219/10.55 R |
| 4,671,935 | 6/1987 | Rohrer et al. | 422/21 |
| 4,703,149 | 10/1987 | Sugisawa et al. | 219/10.55 E |
| 4,889,693 | 12/1989 | Su et al. | 422/133 |
| 4,956,155 | 9/1990 | Rohrer et al. | 422/297 |
| 4,971,773 | 11/1990 | Rohrer et al. | 422/307 |

Primary Examiner—Robert J. Warden
Assistant Examiner—Theresa A. Trembley
Attorney, Agent, or Firm—James B. Bieber; John S. Norton

[57] ABSTRACT

An apparatus for disinfecting contact lenses by use of microwave energy is disclosed wherein a disinfecting fluid is stored in a first chamber and transferred to a second compartment when exposed to microwave energy. The second compartment holds the lenses to be disinfected and is shielded by a microwave deflecting substance.

10 Claims, 3 Drawing Sheets

APPARATUS FOR DISINFECTING CONTACT LENSES USING MICROWAVE ENERGY

BACKGROUND OF THE INVENTION

1. Field of the Invention

This invention relates to disinfecting contact lenses and, more particularly, relates to a method and apparatus for disinfecting contact lenses using microwave energy.

2. Description of Background Art

During the normal course of wearing contact lenses, various debris, organic matter, and microorganisms have a tendency to deposit and/or build up on lens surfaces. Contact lenses, especially those made from hydrophilic materials, must be continuously disinfected to kill any harmful microorganisms that may be present on or grow on the lenses. If the harmful microorganisms are not controlled, corneal infections are a possibility.

Accordingly, a number of methods for disinfecting contact lenses have been used such as the use of elevated temperatures, oxidative chemicals and antimicrobial agents. This invention disinfects through the use of elevated temperatures.

Heat disinfection typically involves inserting the lenses in an electrical device which uses electrical energy to obtain the thermal energy necessary to elevate the temperature of the disinfection fluid. These devices typically employ temperatures of about 70° C. to 90° C. and requires operating cycles from about 20 to 60 minutes. Thus, due to the long period required for heat disinfecting, a shorter more convenient process for heat disinfecting contact lenses is highly desirable.

The desirability of using microwave energy for heat disinfecting contact lenses has been previously discussed. In fact, one patent discloses a technique for disinfecting contact lenses in microwave ovens. U.S. Pat. No. 4,671,935 discloses a method and apparatus for sterilizing contact lenses when the lenses are moved in a circular orbit within a microwave oven with the orbit movement being spaced from the floor of the oven. However, this patent does not employ a disinfecting solution.

Other patents disclose various apparatus used for heating water in microwave ovens for various purposes. For example, U.S. Pat. No. 4,400,357 discloses a device for sterilizing medical and dental objects. U.S. Pat. No. 4,642,443 discloses an apparatus for brewing coffee in microwave ovens. Last, U.S. Pat. No. 4,386,109 discloses a microwave expresso coffee maker. However, none of the aforementioned patents have the same requirements of the present invention and thereby can employ devices which are unsuitable for disinfecting contact lenses. More specifically, none of the aforementioned patents require maintaining the disinfecting temperature for a time sufficient to disinfect while protecting the object to be disinfected from degradation or destruction by microwaves.

Accordingly, the present invention provides a convenient method and apparatus for disinfecting contact lenses using microwave energy. Further, the present invention provides for a short disinfecting period which is more convenient for the contact lens wearer and thereby promotes better contact lens care compliance.

SUMMARY OF THE INVENTION

The present invention provides several embodiments of an apparatus for disinfecting contact lenses using microwave energy, one embodiment comprising:
an outer chamber for holding a fluid,
an inner compartment containing the contact lenses positioned within the outer chamber and capable of being affixed thereto and enclosed therein, wherein the inner compartment has means for substantially restricting the microwave energy from contacting the contact lenses, and
means for transferring the fluid from the outer chamber to the inner compartment when the temperature and pressure of the fluid is elevated by the microwave energy.

A method for disinfecting contact lenses is also provided.

BRIEF DESCRIPTION OF THE DRAWINGS

The invention will be more fully understood by reading the description of one embodiment of the present invention with reference to the drawings wherein.

DETAILED DESCRIPTION OF THE INVENTION

The present invention is a method and apparatus for use with contact lenses which require daily disinfection to kill harmful or pathogenic microorganisms. Typical contact lenses include soft, rigid gas permeable, and silicone lenses. Soft lenses, such as those commonly referred to as hydrophilic or hydrogel lenses, are typically prepared from monomers such as hydroxyethylmethacrylate, hydroxyethylmethyl methacrylate, vinylpyrrolidone, glycerolmethacrylate, methacrylic acid or acidesters and the like and are particularly useful in the present invention. While hard or rigid lenses such as those made from acrylic esters such as polymethymethacrylate and the like do not require daily disinfection, the present invention can also be used to disinfect these lenses.

The present invention employs microwave energy, such as is available from conventional microwave ovens, to heat the disinfecting fluid employed herein. Typically, the microwave energy uses that portion of the electromagnetic spectrum having wave lengths in the region from the far infrared to the short-wave radio wave lengths, typically from one millimeter to three meters and preferably will be about 2450 megahertz which is the frequency typically used in consumer microwave ovens.

The disinfecting fluid of the present invention is typically an aqueous solution containing substantially no or few active ingredients. While for some applications tap or distilled water can be employed, it is preferred that the fluid be a sterile, isotonic, aqueous solution having a pH of about 6.5 to about 8.0 and being osmotically equivalent to lacrimal fluid (equivalent to about 0.8 to about 1.2% sodium chloride). Sodium chloride, potassium chloride, dextrose, glycerin, propylene glycol and various other well known agents can be used to adjust the tonicity of the fluid. Buffering agents may also be used to adjust the tonicity of the fluid as well as to adjust the pH of the fluid. Typical buffering agents are well known in the ophthamtic art and include, but are not limited to, boric acid, phosphoric acid, potassium and sodium bicarbonates, carbonates, citrates, and phosphates; and sodium acetate, borate and phosphate.

The disinfecting fluids can also contain surfactants, preservatives and antimicrobial agents as are commonly known in the art. Hypotonic or hypertonic solutions can optionally be employed as the disinfecting fluid which may have an effect on the disinfecting time and temperature used. Preferably, conventional saline or disinfecting solutions are employed as the disinfection fluid.

It is essential that the boiling point of the fluid be sufficiently high enough to ensure that the contact lenses are in contact with the fluid at disinfecting temperatures. Disinfection of the contact lenses occurs when at least a substantial portion of the microorganism population affixed to the lenses is reduced.

Figure 1:
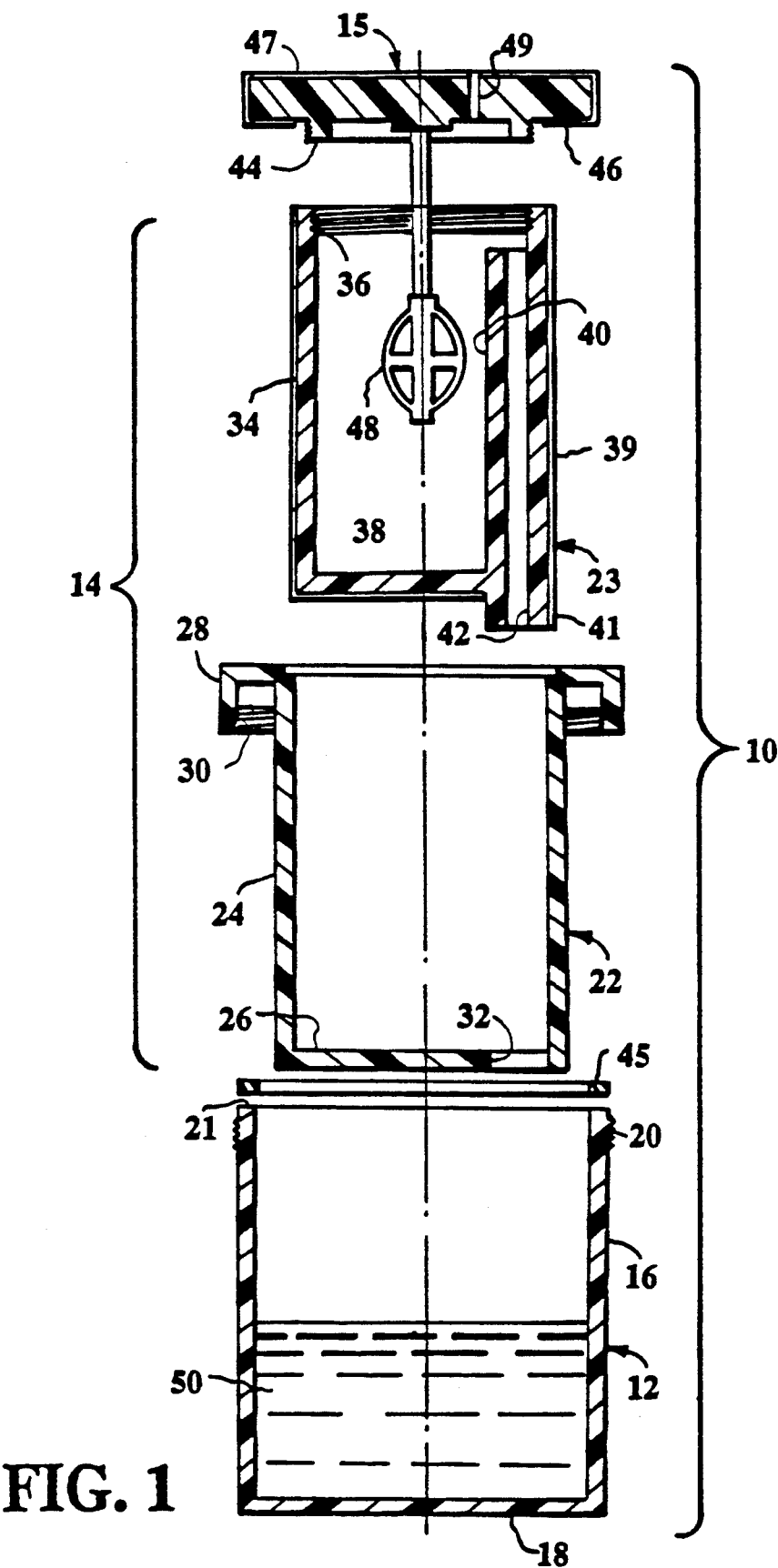
FIG. 1 is an exploded sectional view of the present apparatus for disinfecting contact lenses using microwave energy.
Figure 2:
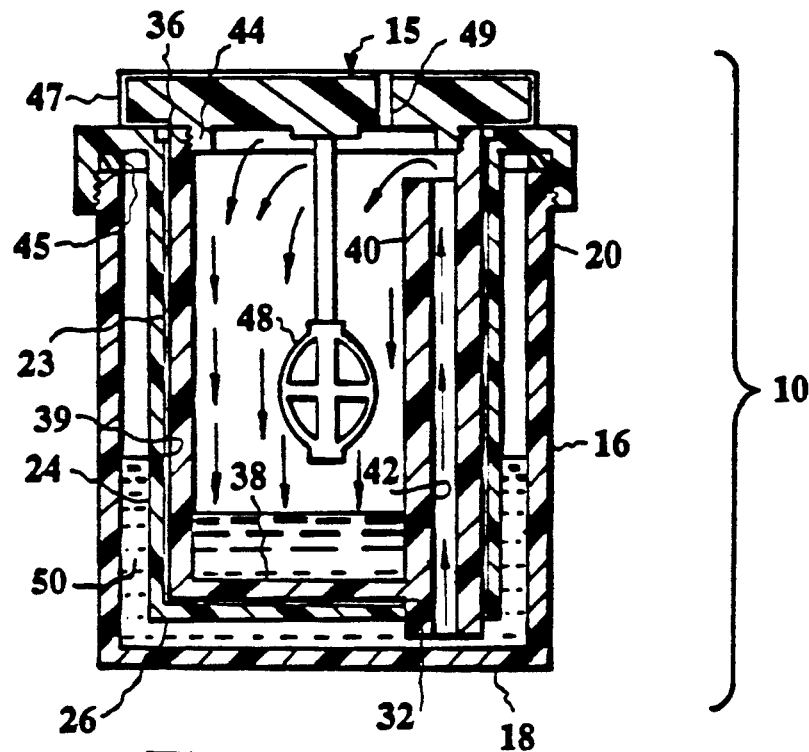
FIG. 2 is an assembled view of the apparatus of FIG. 1.

Referring now to the drawings, FIGS. 1 and 2 illustrate one embodiment of the present invention with numeral 10 denoting generally, the apparatus which contains an outer chamber 12, an inner compartment 14 and a cap 15.

Outer chamber 12 is generally cylindrical with a side wall 16 and a bottom 18. A threaded portion 20 is formed about the upper periphery of side wall 16. Inner compartment 14 includes first and second inner cylindrical chambers 22 and 23, respectively, with a microwave energy deflecting substance 39, such as conventional metals (e.g. aluminum) applied between the chambers 22 and 23. The chambers are joined together by, for example, an adhesive or by ultrasonic welding. First inner chamber 22 has a side wall 24 and a bottom 26 having an aperture 32. A flange 28 is formed on side wall 24 at the upper periphery thereof and includes a threaded portion 30. An annular gasket 45 is sized to seat between flange 28 of first inner chamber 22 and the rim 21 of outer chamber 12. The second inner chamber 23, as in the previously described chamber, has a side wall 34 having a threaded portion 36 and bottom 38. Side wall 34 includes a rib 40 which is integrally formed on an interior surface of the chamber side wall and extends through bottom 38 to form a stub portion 41. Stub 41 is dimensioned so as to closely fit through aperture 32 of first inner chamber 22. The rib 40 includes a passageway 42.

Last, cap 15 includes a threaded annular boss 44 and a contact lens support basket 48 affixed to, and suspended from, its underside 46. Additionally, a microwave deflecting substance 47, similar to substance 39, is provided about cap 15. Deflecting substance 47 may be eliminated if the microwave energy is incapable of penetrating compartment 14 sufficiently to come in contact with the lenses or spent disinfecting fluid. A pressure relief aperture 49 is provided through the cap.

In operation, the contact lens disinfecting apparatus is broken down into its previously described constituent parts and a suitable amount of an appropriate disinfecting fluid 50 is poured into outer chamber 12. Inner compartment 14, which as mentioned previously consists of first and second inner chambers 22 and 23, is thereafter inserted into the outer chamber 12 and secured thereto by the mating of threaded portions 20 and 30 and sealed by gasket 45. The contact lenses to be disinfected are then placed in the contact lens basket 48 suspended from the underside 46 of cap 15, which is then secured to the inner chamber 12 by way of mating threaded portions 36 and 44. Obviously, other means can be used to hold the lenses in proper position for disinfecting.

The assembled disinfecting apparatus 10 is then inserted into a conventional microwave oven. Appropriate time and heat settings are selected and the oven is energized. The microwave energy produced by the oven penetrates the outer chamber 12 and causes the temperature of the disinfecting fluid 50 to rapidly rise until such time that the internal pressure within outer chamber 12 rises sufficiently to force the heated disinfecting fluid 50 to migrate up passageway 42 where it contracts and is deflected by the underside 46 of cap 15. The fluid deflection is such that it, in effect rains down over the lenses suspended in basket 48 and subsequently collects in the bottom of second inner chamber 23. However, the microwave deflecting substances 39 and 47, provided about second inner chamber 23, and cap 15, respectively, prevent any microwave energy from penetrating the second inner chamber 23 and reheating the collected fluid. This could have a deleterious effect on the lenses by causing them to degrade.

As previously described, once the disinfecting fluid 50 is transferred from the outer chamber 12 to the inner compartment 14, it is no longer exposed to the microwave energy due to the deflecting substances incorporated in the inner chamber and, optionally, the cap 15. Therefore, although the microwave energy may continue to be transmitted after the fluid transfer has been effected, the cool down cycle of the disinfecting fluid has already begun. Optionally, outer chamber 12 may be constructed of a clear material which would enable the user to visually determine if the fluid 50 has been transferred to the inner compartment 14. The pressure relief aperture 49 has been provided in cap 15 to ensure that no dangerous pressures are allowed to build within the disinfecting apparatus during the disinfecting process. Alternatively valves can be employed to release excess pressure as necessary.

Figure 3:
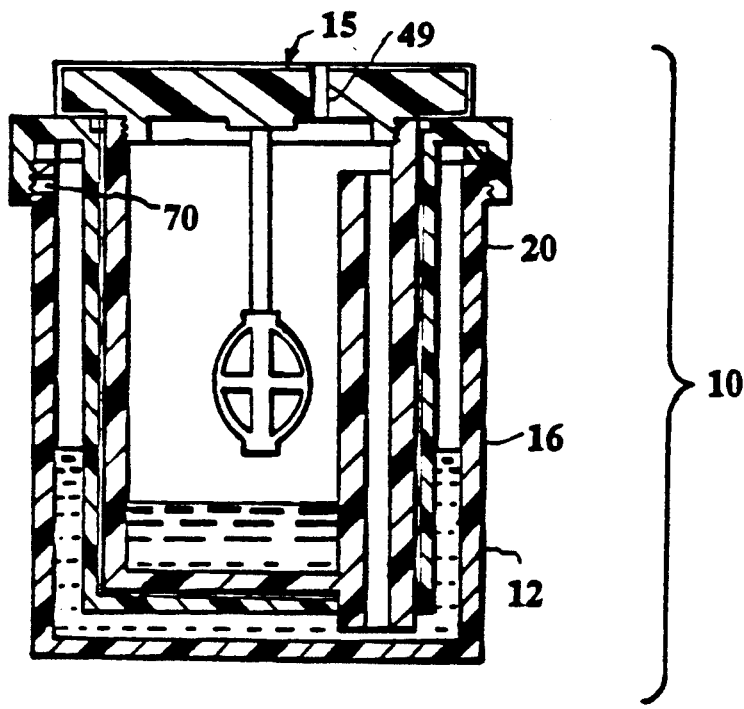
FIG. 3 is a sectional view of an alternate embodiment of the invention.

In an alternate embodiment of the present invention, as shown in FIG. 3, outer chamber 12 is provided with an aperture 70 through threaded portion 20 of side wall 16. Aperture 70 slows the rate at which the pressure increases in the outer chamber 12 by allowing some of the pressure to escape to the atmosphere. Accordingly, as pressure escapes through aperture 70, the pressure increase in outer chamber 12 is slowed and the temperature at which the disinfecting fluid 50 transfers to inner compartment 14 is higher. In other words, the rate of the pressure increase is slowed through the partial release of gases through aperture 70 resulting in an extended time period being required before the pressure and temperature of the disinfecting fluid 50 increase to the point necessary for transfer to inner compartment 14. This extended time period also results in an extended contact time between the disinfecting fluid 50 and the microwave energy. Accordingly, the final temperature of the disinfecting fluid 50 will be increased when it comes in contact with the lenses. As a final result of the use of aperture 70, the transfer of disinfecting fluid 50 from outer chamber 12 to inner compartment 14 can be controlled which, in turn, controls the contact lens disinfecting cycle. Obviously, the size of aperture 70 is selected to allow venting of pressure, without preventing the solution from transferring into second inner chamber 23 of compartment 14.

Accordingly, the embodiments of the present invention described above advantageously preheat the outer wall of the inner compartment 14 to optimize the disinfecting process. The design of the present invention which includes the shielding of inner compartment 14 in conjunction with the systematic increase in the pressure and temperature of outer chamber 12 combine to provide an effective control of the disinfecting parameters necessary to optimize the disinfecting process. It is important to note that during the operation of the present invention, the disinfecting temperatures are provided to the contact lenses directly from the disinfecting fluid 50 rather than from the microwave energy. This mode of operation promotes better control of the disinfecting process while protecting the contact lenses from user error.

Figure 4:
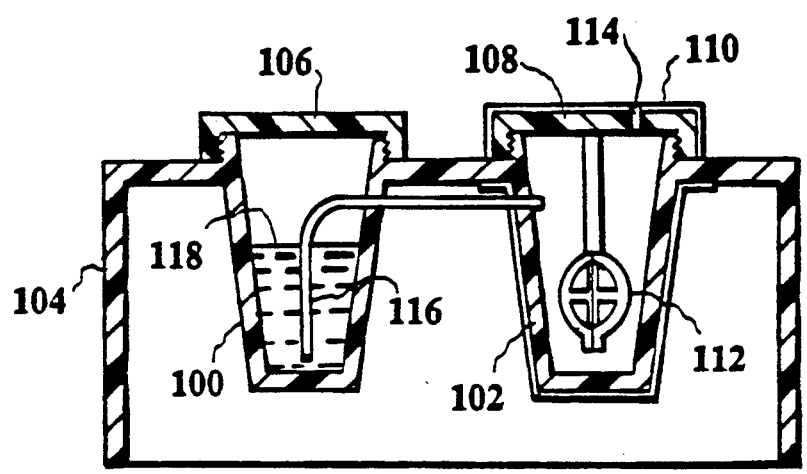
FIG. 4 is a sectional view of another alternate embodiment of the invention.

A still further embodiment of the present invention is shown in FIG. 4. In this embodiment a pair of chambers 100 and 102 are disposed in a side-by-side relationship in a support frame 104. Sealing member, such as a cap 106 is sealingly engaged to chamber 100, while a similar cap 108 is affixed to chamber 102. A microwave deflecting substance 110 is disposed about both chamber 102 and, optionally, cap 108. Substance 110 also extends partially into support frame 104. A contact lens support basket 112 is suspended from the underside of cap 108. A aperture 114 is formed through cap 108. A solution transfer tube 116 is disposed as shown, so as to be in communication with the interiors of both chambers 100 and 102, respectively.

In operation, the apparatus of this embodiment operates in the following manner. Cap 106 is removed from chamber 100 and a preselected amount of fluid 118 is introduced thereto. Cap 106 reaffixed to chamber 100. Cap 108 is then removed from chamber 102, the contact lenses to be disinfected are placed in support basket 112 and the cap reattached to the chamber 102.

The assembled unit is then placed in a typical microwave oven. The oven is set to preselected heat and temperature ranges and energized. The microwave energy penetrates chamber 100 and heats the fluid. As in the previously described embodiments, as the temperature and pressure increases the heated fluid 118 migrates through transfer tube 116 from chamber 100 to chamber 102. The transferred heated fluid 118 recollects in chamber 102 to a level such that the contact lenses held in support basket 112 are submerged in the fluid. However, as in the previously described embodiments, chamber 102 is protected by a microwave deflecting substance 110, the fluid collected in the chamber is not subjected to further heating.

The operation of the present invention occurs as follows. Prior to disinfection, the lenses are removed from the wearer's eye and, preferably cleaned in the conventional way to remove debris and deposits on the lenses. Typically, the wearer will clean the lenses with a daily cleaner and, according to the recommended lens care regimen, with a protein removing cleaner. The cleaned lenses are then placed into the support baskets. A preselected amount of the disinfecting fluid 50 is placed into outer chamber 12 or chamber 100 and the component parts of the apparatus are secured together. The apparatus is placed into the approximate center of a conventional consumer microwave oven and heated for the appropriate time. After heating, the apparatus is, preferably, left to cool in an unopened state for several minutes. Thereafter, the lenses can be placed directly in the eye. Optionally, a saline rinse can be used prior to insertion.

It should be understood that the scope of the subject invention is not limited to the examples set forth above, but includes equivalent embodiments, modifications and variations that fall within the scope of the attached claims.

What is claimed is:

1. An apparatus for disinfecting contact lenses using microwave energy comprising:
   an outer chamber for holding a disinfecting fluid,
   an inner compartment containing contact lenses positioned within said outer chamber and capable of being affixed thereto and enclosed therein, wherein said inner compartment has means for substantially restricting microwave energy form contacting said contact lenses; and
   means for transferring disinfecting fluid, held within said disinfecting outer chamber, from said outer chamber to said inner compartment when the temperature and pressure of said fluid is elevated by microwave energy.

2. The apparatus set forth in claim 1 wherein said means for substantially restricting microwave energy comprises a microwave deflecting substance effectively applied to said inner compartment so as to prevent said microwave energy from penetrating said inner compartment.

3. The apparatus as set forth in claim 1 wherein said transfer means comprises a passageway formed in said inner compartment and in communication with said outer chamber.

4. The apparatus as set forth in claim 1 wherein said outer chamber and said inner compartment are detachably joined together.

5. An apparatus for disinfecting contact lenses using microwave energy comprising:
   an outer chamber capable of holding a disinfecting fluid;
   an inner compartment, capable of housing contact lenses positioned within the outer chamber and detachably affixed thereto;
   means for enclosing said inner compartment and said outer chamber and for directly restricting disinfecting fluid in said outer chamber from flowing into the environment; and
   means for transferring disinfecting fluid, held within said outer chamber, from said outer chamber to said inner compartment when the temperature and pressure of said disinfecting fluid is elevated by microwave energy.

6. The apparatus as set forth in claim 5, wherein said enclosing means includes a cap which is detachably secured to said inner compartment.

7. The apparatus as set forth in claim 6, wherein said cap includes means thereon for suspending said contact lenses within said inner compartment.

8. The apparatus as set forth in claim 5, wherein said inner compartment comprises first and second inner cylinders coaxially joined together with means for deflecting microwave energy being mounted there between.

9. The apparatus as set forth in claim 8, wherein said disinfecting fluid transfer means comprises a passageway formed in said second inner cylinder and communicating through said first inner cylinder to said outer chamber.

10. The apparatus as set forth in claim 5 wherein said outer chamber is formed of a clear material for visually determining when the disinfecting fluid has transferred from said outer chamber to said inner compartment.

* * * * *

UNITED STATES PATENT AND TRADEMARK OFFICE
CERTIFICATE OF CORRECTION

PATENT NO. : 5,164,166
DATED : November 17, 1992
INVENTOR(S) : Stephen F. Stefanski, et al It is certified that error appears in the above-indentified patent and that said Letters Patent is hereby corrected as shown below:

On the title page, Item [75], the inventor's name is misspelled. In both instances where it appears, it should be "Stefanski", not "Stepanski".

In column 6, line 15, change "form" to "from" after "microwave energy".

Signed and Sealed this

Eighteenth Day of January, 1994

Attest:

BRUCE LEHMAN

*Attesting Officer*     Commissioner of Patents and Trademarks